United States Patent [19]
Svec

[11] Patent Number: 5,851,549
[45] Date of Patent: Dec. 22, 1998

[54] PATCH, WITH SYSTEM AND APPARATUS FOR MANUFACTURE

[75] Inventor: James A. Svec, Bloomingdale, N.J.

[73] Assignee: Becton Dickinson and Company, Franklin Lakes, N.J.

[21] Appl. No.: 549,747

[22] PCT Filed: May 25, 1994

[86] PCT No.: PCT/US94/05861

§ 371 Date: Apr. 23, 1996

§ 102(e) Date: Apr. 23, 1996

[87] PCT Pub. No.: WO94/27649

PCT Pub. Date: Dec. 8, 1994

[51] Int. Cl.[6] .............................. A61F 13/00; B32B 31/00; A61K 9/70

[52] U.S. Cl. ........................... 424/448; 424/449; 156/252

[58] Field of Search ................................ 424/448, 449; 156/252

[56] References Cited

U.S. PATENT DOCUMENTS 4,556,441  12/1985  Faase, Jr. ............................... 156/247
4,666,441   5/1987  Andriola et al. ........................ 604/897
5,064,422  11/1991  Wick ....................................... 604/307
5,503,843   4/1996  Santus et al. ........................... 424/448

Primary Examiner—Joseph L. Schofer
Assistant Examiner—Kathryne E. Shelborne
Attorney, Agent, or Firm—Hoffmann & Baron, LLP

[57] ABSTRACT

A system of the present invention for applying a substance to an applied area includes a patch (11), as well as apparatus (12, 14, 16, 18 and 21) and methods for making the same. The patch includes backing material (52) and a tri-laminate (54), with a dose of medication sealed therebetween in reservoir (62). To facilitate and increase transdermal and/or topical application of the medication to the applied area, such as the skin of a user, the tri-laminate includes a layer material (68) having at least one opening therein (64), which permits the medication to flow through each opening without tearing or ripping the layer of material covering the reservoir.

20 Claims, 11 Drawing Sheets

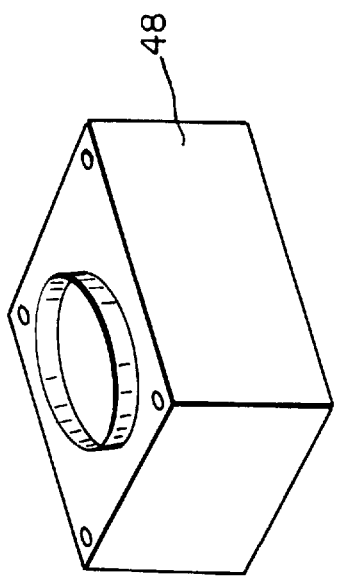
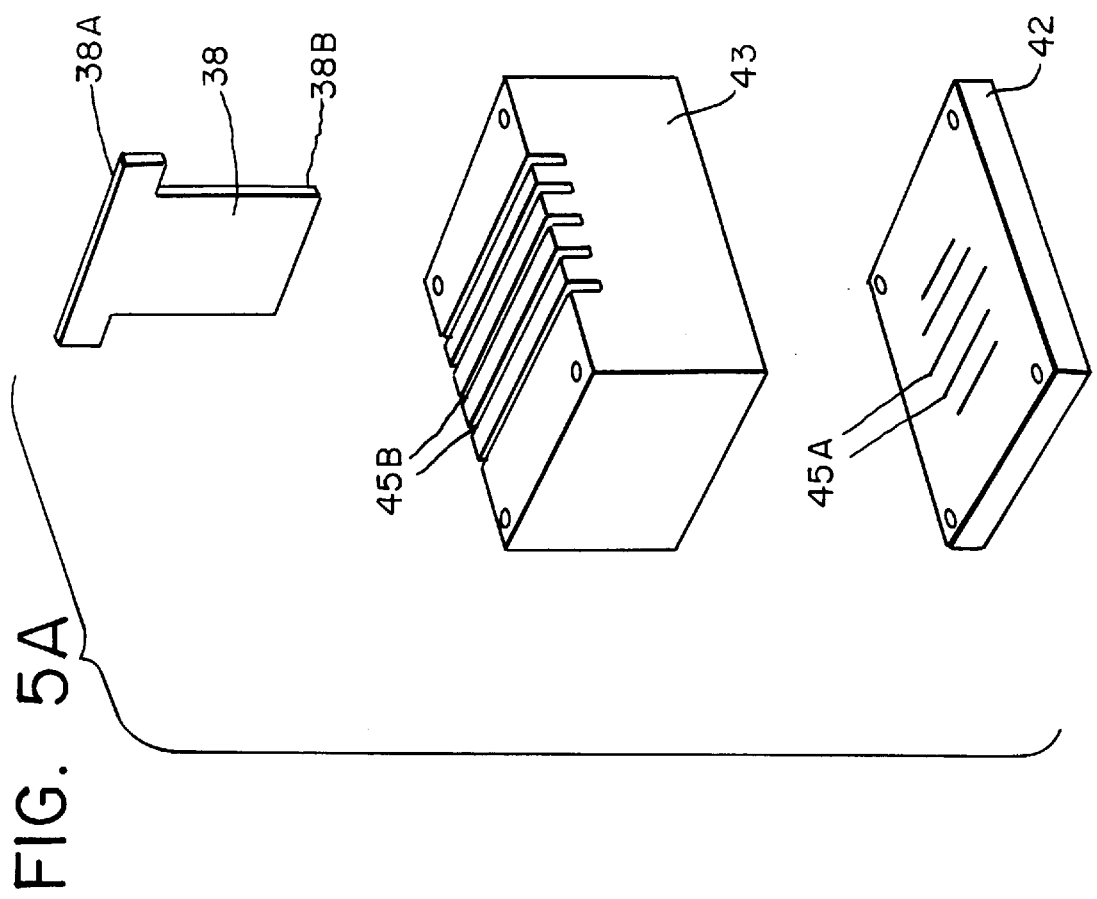

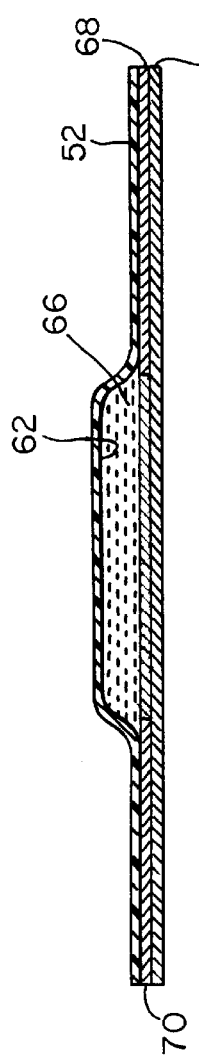
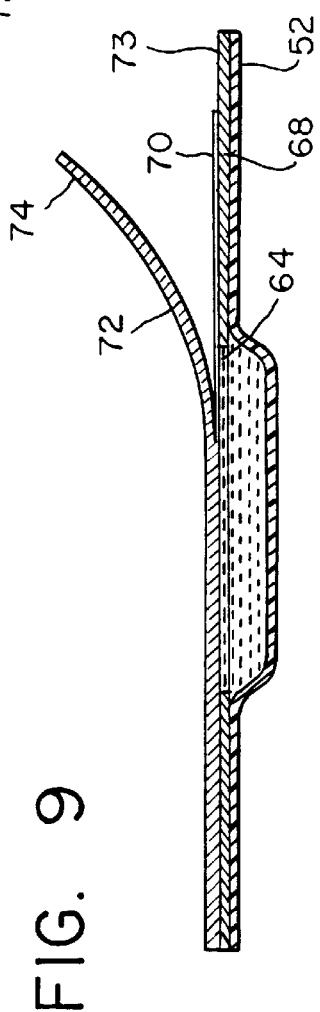
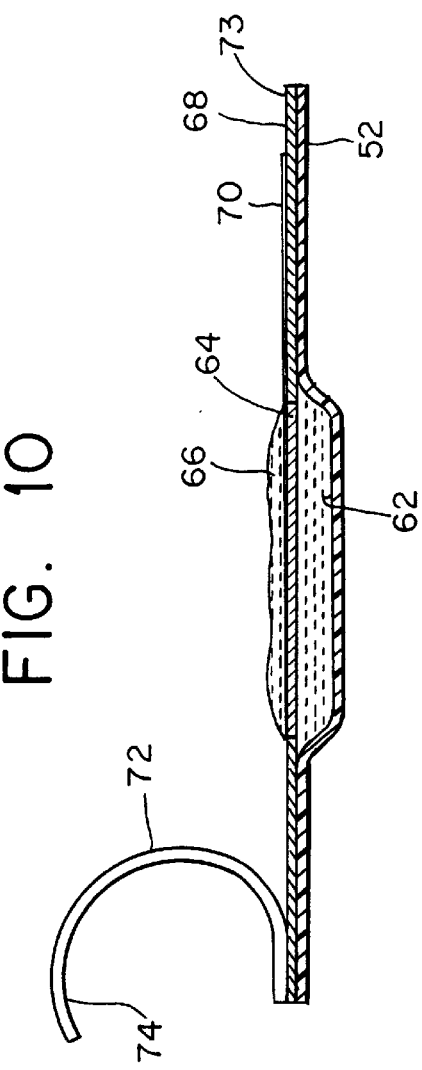
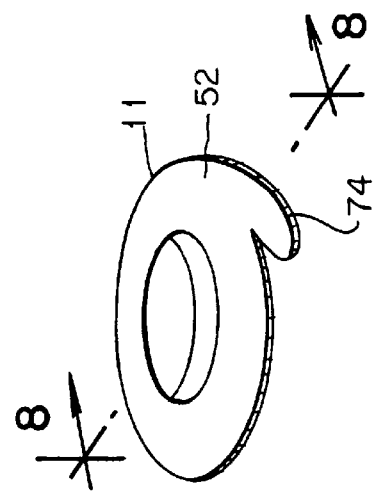
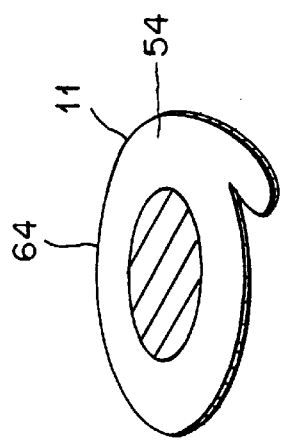

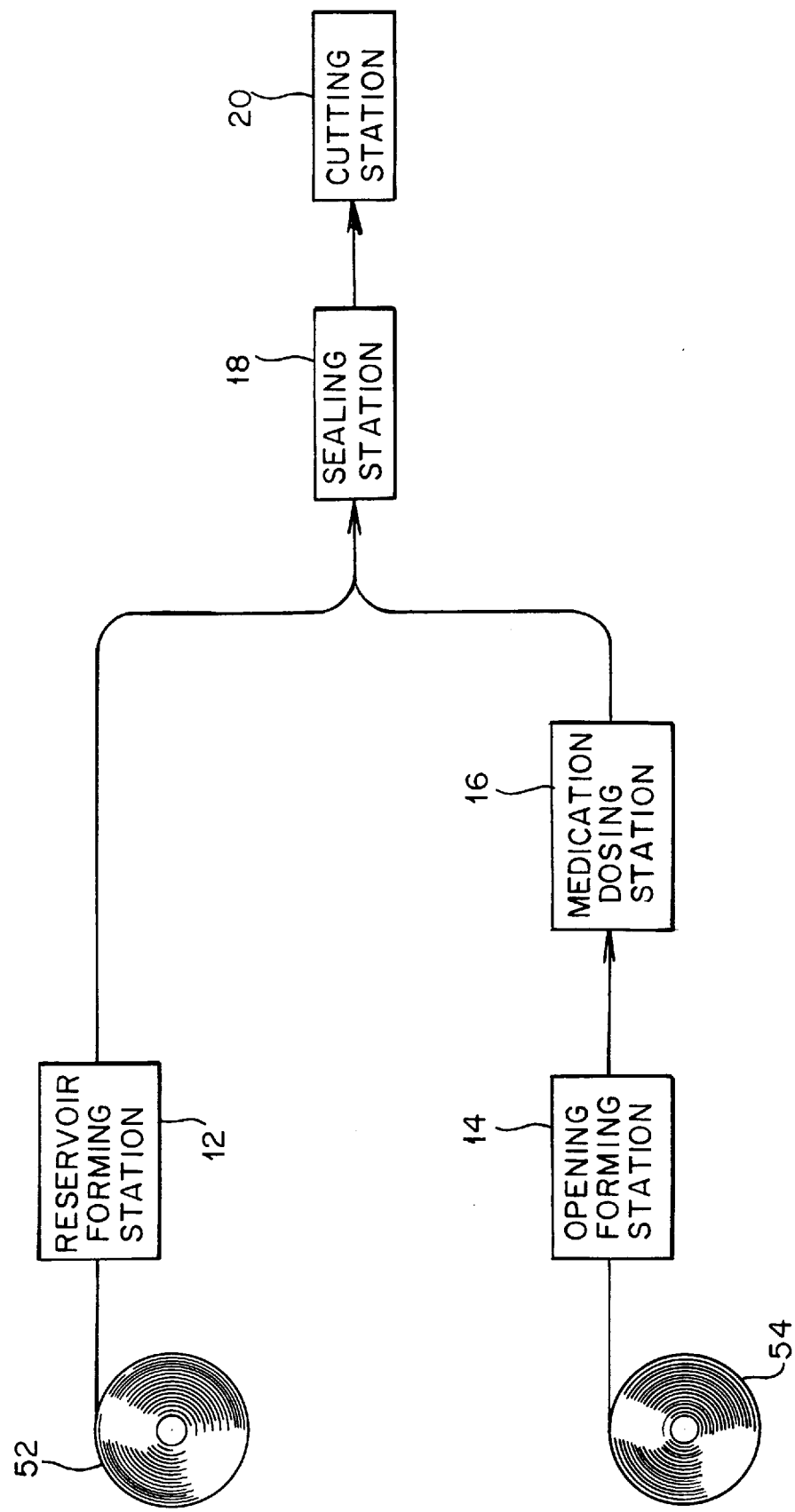

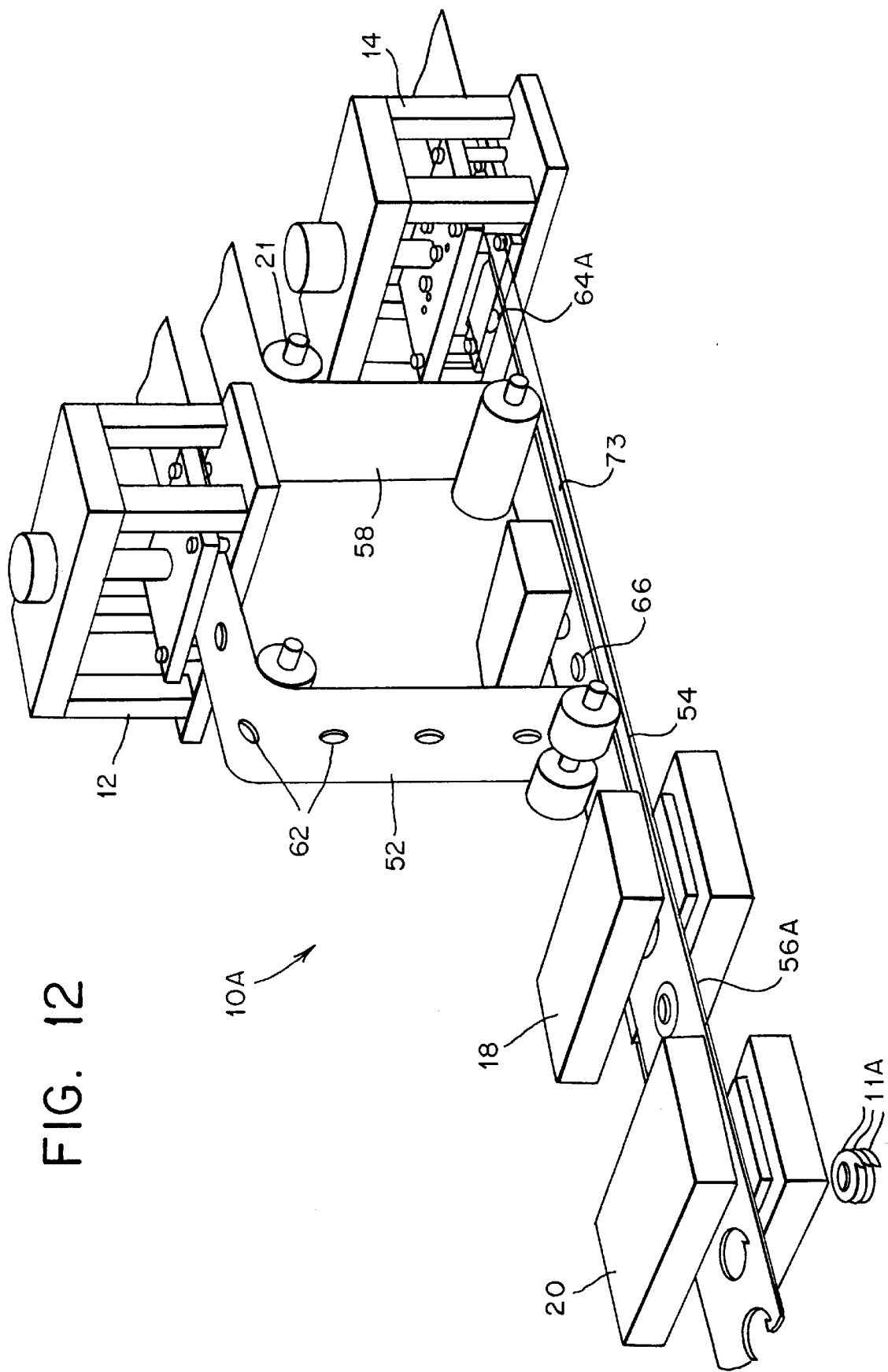

5,851,549

PATCH, WITH SYSTEM AND APPARATUS FOR MANUFACTURE

FIELD OF THE INVENTION

The present invention relates generally to systems for applying substances and, specifically, to a system, including a patch, for applying transdermally and/or topically deliverable substances such as medications to a localized area of a patient such as a point of irritation, injury, infection and the like while preventing excess medication from being applied to the area, and an apparatus and method for making such a drug delivery system.

BACKGROUND OF THE INVENTION

Transdermal drug delivery systems have, in recent years, become an increasingly important means of administering drugs. Such systems offer advantages clearly not achievable by other modes of administration such as avoiding introduction of the drug through the gastro-intestinal tract or punctures in the skin to name a few. An example of which involves the application of a topical anesthetic to provide localized relief, as disclosed in U.S. Pat. No. 3,814,095 (Lubens).

A variety of transdermal drug delivery systems or patches are commercially available and well known in the art. One such system is known as the TTS Nitro™ patch (Ciba Geigy). Such a patch includes a reservoir containing the medication, which is in the form of a viscous substance. The patch also includes a backing material which can be peeled away and discarded prior to topical application of the patch. In addition, the patch includes a size exclusion membrane covering the medication, which comes in contact with the area to which the patch is applied. The membrane also maintains the medication in the patch and permits passage of the medication through the membrane into the applied area. However, problems and limitation have been associated with such patches, including limits on the rate of delivery of the medication, i.e., nitroglycerine, as a result of the permeability of the membrane.

Thus, there has been a need for a system for applying substances such as medications to an applied area, wherein the rate of delivery of the medication is limited only by the permeability of the area to which the patch is applied. In addition, there has been a need for an apparatus and a method of making such a patch.

SUMMARY OF THE INVENTION

In contrast to the prior systems discussed above, it has been found that a system including a patch for transdermally and/or topically applying a substance such as a medication can be constructed in accordance with the present invention. In addition, the patch is easily activated by the user to administer the medication, which can be forced from the patch and located or otherwise situated at the area to be applied. Such users may include the patient as well as doctors, nurses and the like.

The patch of the present invention for applying a substance such as a transdermal medication topically to an applied area includes a first material having a reservoir formed therein, a dosage of medication contained in the reservoir, and a second material covering the reservoir with at least one opening formed therein through which the medication may pass for application to the applied area. In the preferred embodiment, the patch also includes a porous material situated between the second material and the dose of medication. The porous material may include a layer of non-woven material. In addition, the second material includes a layer of an adhesive material and a release liner covering the layer of adhesive material with the adhesive material sandwiched between the release liner and the diaphragm, with at least either the first material or the second material includes a heat seal coating. Further, the reservoir is defined by a dimple formed in the first material with a cavity therein.

In an alternative embodiment of the patch, the second material includes a diaphragm and wherein-the at least one opening includes a plurality of slits formed in the diaphragm.

The method of the present invention of making a patch for topically applying a substance to an applied area of a patient includes the steps of forming a reservoir in a backing material, cutting at least one opening in at least a portion of a tri-laminate material, placing a dose of medication on the tri-laminate material approximate the at least one opening, sealing the backing material and the tri-laminate material together to form a continuous web, and cutting a patch from the web.

In the preferred embodiment, the method also includes the step of placing a porous material between the tri-laminate material and the backing material prior to placing the dose of medication on the tri-laminate material so that the porous material is situated between the dose of medication and the tri-laminate material, with the porous material including feeding a layer of non-woven material therebetween. In addition, the step of sealing the backing material to the tri-laminate material incudes the step of forming a heat seal around a periphery of the reservoir. Also, the step of cutting the patches from the continuous web includes die cutting and the step of forming the reservoir in the backing material includes applying a positive pressure to one side of the backing material.

In an alternative embodiment of the method, the step of cutting the opening in the tri-laminate material includes cutting a plurality of slits in a diaphragm.

The apparatus of the present invention for making a patch for applying a substance to an applied area of a patient includes means for forming a reservoir in a backing material, means for cutting at least one opening in a first layer of a tri-laminate material, means for placing at least one dose of medication on the tri-laminate material, means for sealing the backing material and the tri-laminate material together to form a continuous web, and means for cutting a patch from the continuous web.

In the preferred embodiment, the apparatus also includes means for placing a porous material between the tri-laminate material and the dose of medication, with the means for placing the porous material including means for applying a layer of a non-woven material to the tri-laminate material before placing the dose of medication thereon. In addition, the means for cutting the at least one opening includes a bracket assembly and a pair of spacers. Also, the means for cutting the at least one opening is adapted to include at least one adjustment screw for adjusting the cutting edge of the blade.

In an alternative embodiment of the apparatus, the bracket assembly includes at least one blade having a cutting edge for cutting the at least one opening in the first layer of material. In addition, an extending portion of the pair of spacers is aligned with the cutting edge of the blade to limited advancement of the cutting edge and the corresponding depth of the opening in the tri-laminate material.

BRIEF DESCRIPTION OF DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 5A is an exploded perspective view of the bracket assembly for holding one or more blades for forming slits;

FIG. 6 is a perspective view of the patch of the present invention;

FIG. 7 is a perspective bottom view of the patch illustrated in FIG. 6;

FIG. 8 is an enlarged, cross-sectional, side view of the patch illustrated in FIG. 6;

FIG. 9 is an enlarged, fragmentary view of the patch illustrated in FIG. 6 showing removal of the release liner;

FIG. 10 is an enlarged, fragmentary view of the patch illustrated in FIG. 6 showing removal of the release liner with the medication being released or otherwise forced through each opening in the diaphragm from the reservoir;

FIG. 11 is a logic flow diagram depicting the various steps for the method of making the patch of the present invention;

FIG. 12 is a perspective schematic view of the preferred embodiment of the apparatus of the system of the present invention illustrating the various steps for making the patches, including the step of applying a porous material such as a layer of non-woven material to the tri-laminate material prior to placing the dose of medication thereon, and FIG. 12A is a perspective view of the bracket assembly for holding the cutter for forming the opening by kiss-cutting the first layer of the tri-laminate material;

DETAILED DESCRIPTION OF THE PREFERRED EMBODIMENT(S)

Figure 1:
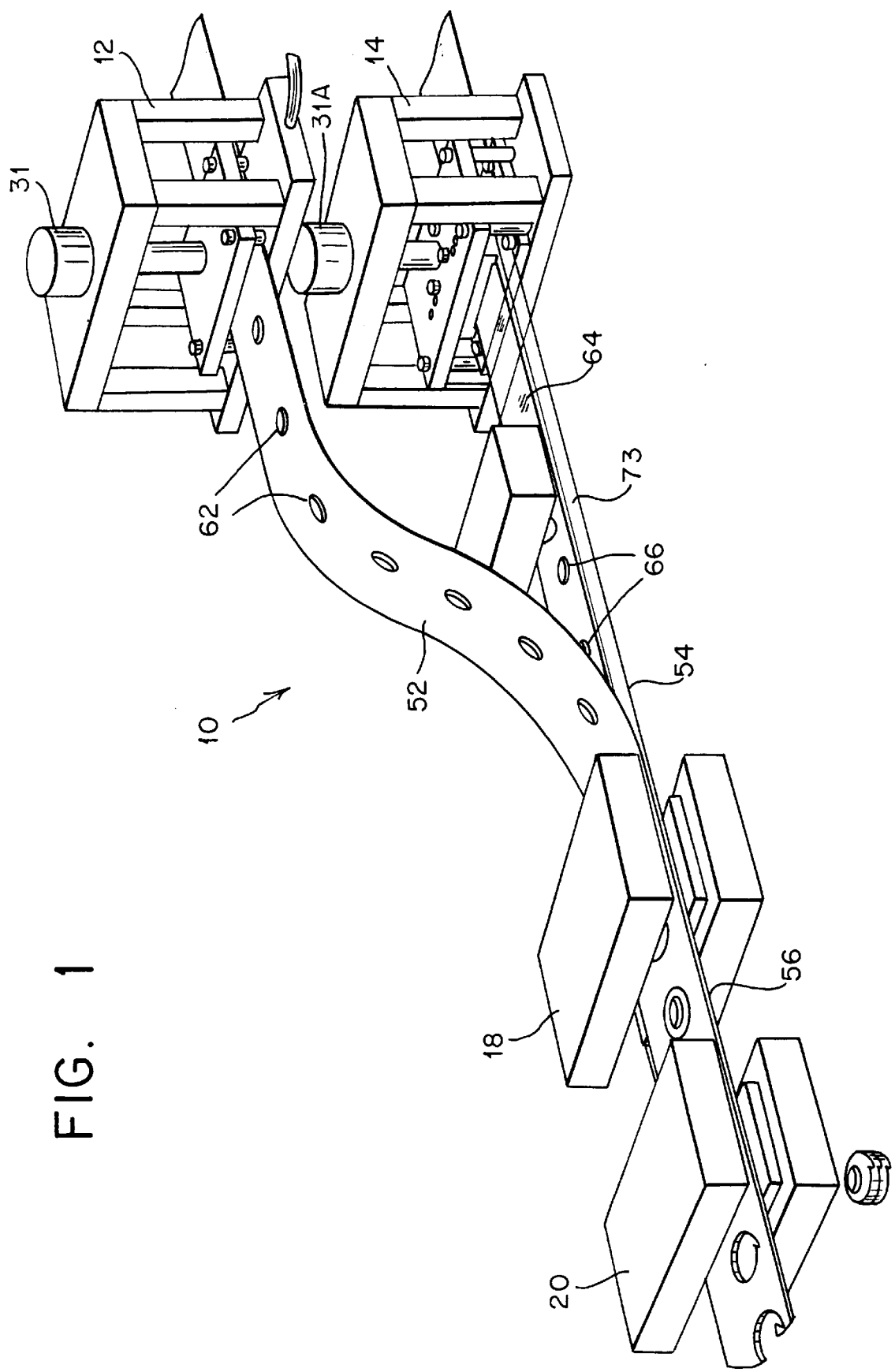
FIG. 1 is a perspective schematic view of the apparatus of the system of the present invention illustrating the various steps for making the patches.

The various embodiments of the system of the present invention for applying a substance to an applied area are illustrated in FIGS. 1–15, with the apparatus generally designated as 10 and the patches generally designated as 11.

Referring to FIG. 1, and FIGS. 2–5 for greater detail, the apparatus 10 of the present invention includes a number of sub-assemblies 12, 14, 16, 18 and 20 for forming a backing material 52 and a tri-laminate material 54 into a continuous web 56 from which the patches 11 are cut. Specifically, the apparatus includes a sub-assembly 12 for forming a reservoir 62 in the backing material 52, a sub-assembly 14 for forming at least one opening 64 in one layer of the tri-laminate material to provide a passage for the substance to be applied, a sub-assembly 16 for placing a dose of the substance such as a medication 66 on the tri-laminate material, a sub-assembly 18 for sealing the backing material and tri-laminate material together with the medication therebetween into the continuous web 56, and a final sub-assembly 20 for cutting the patches 11 from the continuous web.

In one embodiment of the patch 11 illustrated in FIGS. 6–10, the backing material 52 forming one portion of the continuous web is preferably a 2–3 mil thick sheet of Scotch Pack™ film available from Minnesota Mining and Manufacturing Company ("3M"), St. Paul, Minn. Also, the tri-laminate material 54 forming the other portion of the continuous web may include a diaphragm or barrier material 68 for covering the reservoir 62, such as a 3 mil thick sheet of 9% EVA or treated polyester membrane material, a layer of adhesive 70, such as silicone, acrylic or MA 24™ adhesive, and a 1–2 mil thick sheet of polyester film 72 for covering the patch, such as coated polyester with a silicone release coating thereon and a heat seal coating available from Adhesive Research, Glennrock, Pa.

Figure 2:
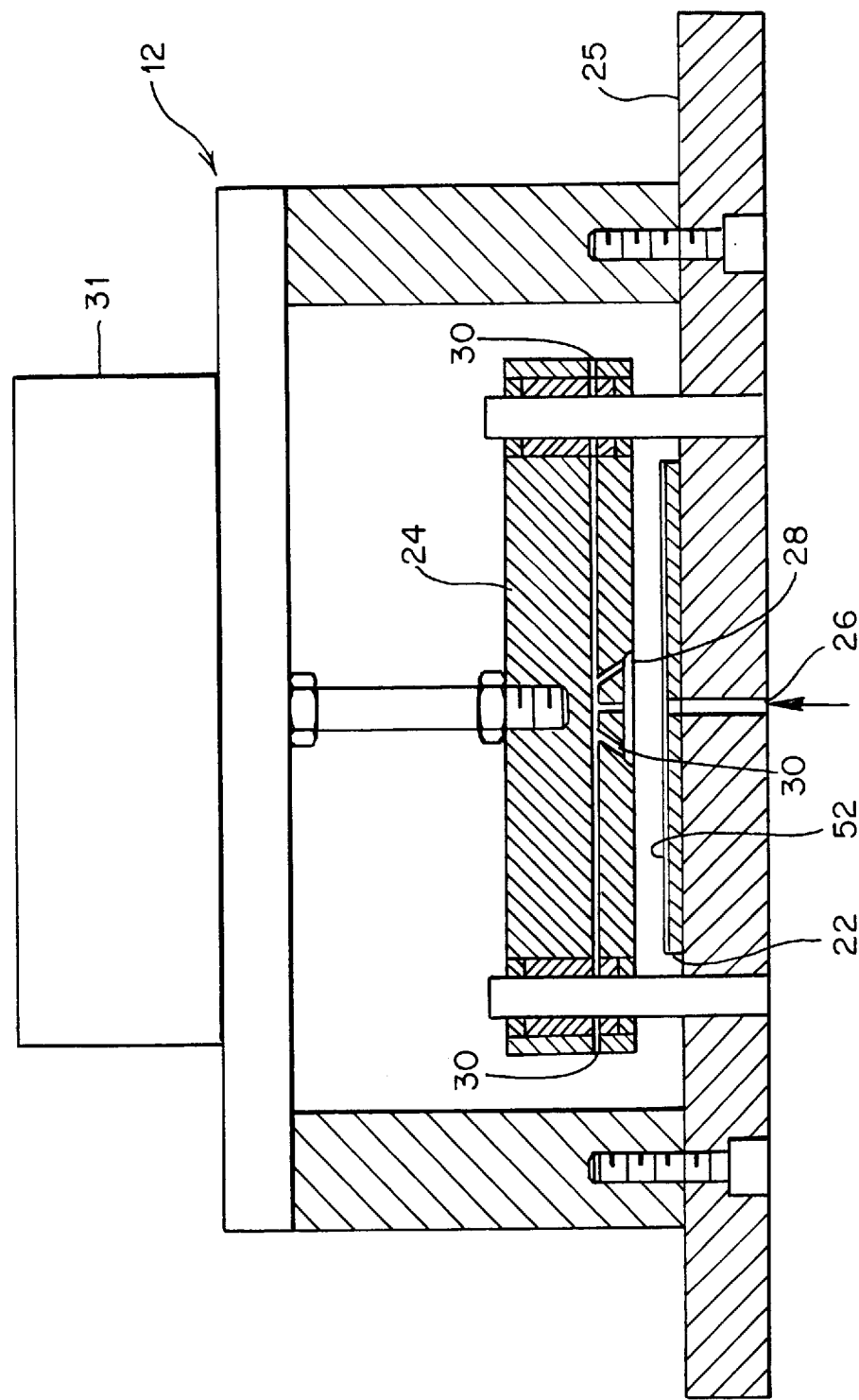
FIG. 2 is a cross-sectional, side view of the sub-assembly for forming the reservoir or dimple in the patch.
Figure 4:
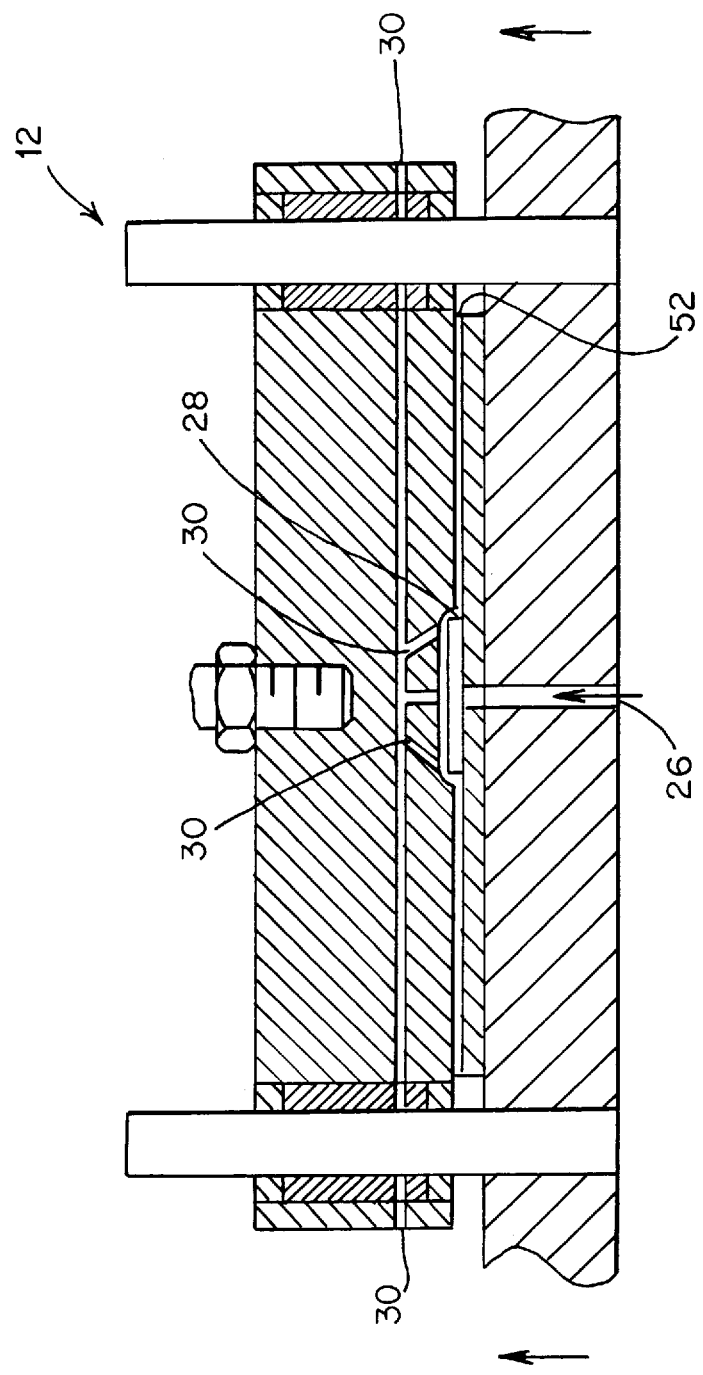
FIG. 4 is an enlarged, fragmentary view of the sub-assembly illustrated in FIG. 2.

As illustrated in FIG. 1, and in greater detail in FIGS. 2 and 4, the sub-assembly 12 for forming the reservoir includes a bottom plate 22 and a top plate 24 mounted to a frame 25, with at least one of the plates being movable in the vertical direction relative to the other plate. At least one channel 26 is formed in the bottom plate 22, and a cavity 28 is formed in the top plate 24, with a number of connecting channels 30 in communication with the cavity and the atmosphere. The backing material passes between the plates 22, 24, which can be brought together by an actuating cylinder and a positive pressure provided through channel 26 against the backing material to force the backing material into the cavity beyond the point of elasticity of the backing material to permanently form a dimple or blister in the backing material, with the amount of pressure being applied depending upon the elastic strength of the backing material, which in the case of the preferred material is 40 to 80 PSI. A vacuum may be drawn on the opposite side of the backing material to facilitate forming of the reservoir.

Figure 3:
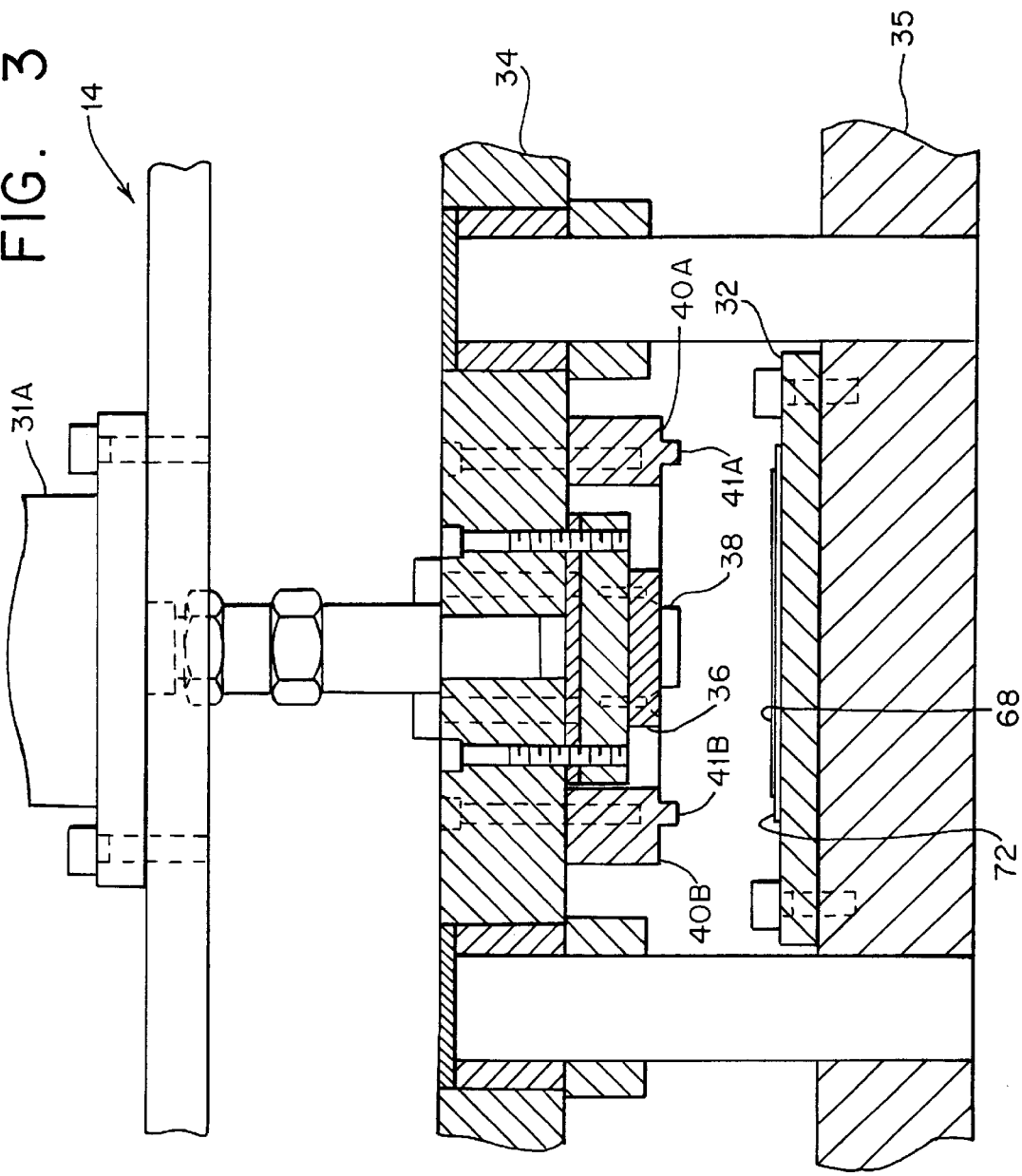
FIG. 3 is a cross-sectional, side view of the sub-assembly for forming at least one opening -in the diaphragm or barrier of the patch.
Figure 5:
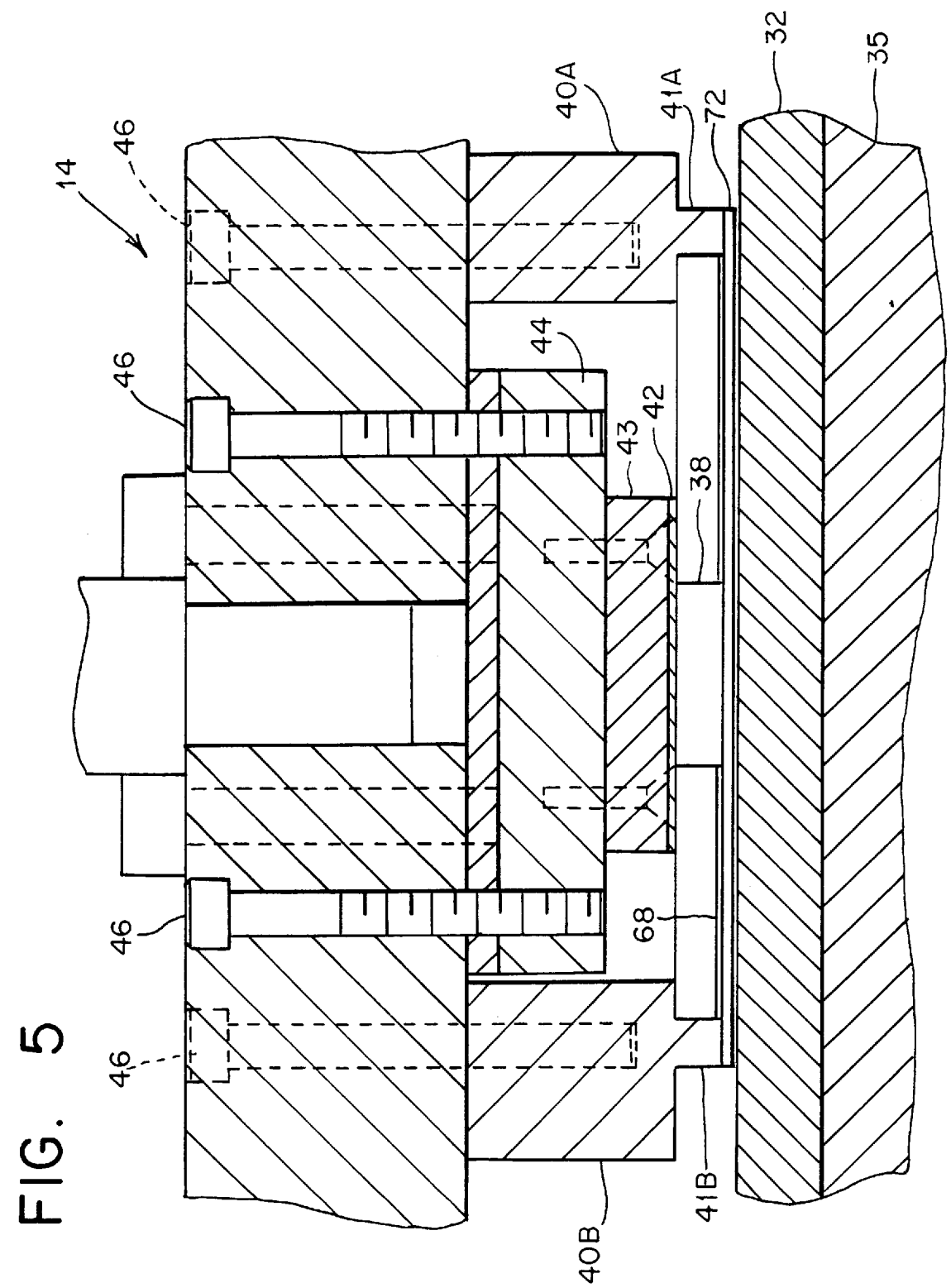
FIG. 5 is an enlarged, fragmentary view of the sub-assembly illustrated in FIG. 3.

As illustrated in FIG. 1, and in greater detail in FIGS. 3, 5 and 5A, the sub-assembly 14 for forming the opening 64 in the tri-laminate material 54 includes a bottom plate 32 and a top plate 34 mounted to a frame 35, with at least one of the plates being movable relative to the other by an actuating cylinder 31A. A bracket assembly 36 is attached to the top plate 34 for holding at least one blade 38, and a pair of spacers 40A and 40B is attached along the sides of the bracket assembly to the frame 35 for limiting advancement of the blade in the tri-laminate material, with the blade 38 being of generally T-shape.

As illustrated in FIGS. 5 and 5A, the bracket assembly 36 is mounted to the top plate 34 and includes a face plate 42, a blade holder 43 and a backing plate 44. The face plate 42 may include a plurality of slits 45A and the blade holder may include a plurality of slits 45B, with the slits 45A and 45B sized to accept each blade therein. Alternatively, each could include slits corresponding to the number of blades utilized. An upper portion 38A of each blade 38 rests against an upper surface 43A of the blade holder 43, with a lower portion 38B of the blade having the cutting edge thereon extending through the face plate 42 to come in contact with the diaphragm 68. In this way, the upper portions 38A of each blade 38 can be ground to provide a level surface in contact with the backing plate 44. In addition, the bracket assembly 36 and the spacers 38A and 38B are adjustable by means of a number of screws 46.

A dose of medication is applied to the tri-laminate material above the opening 64 previously cut in the diaphragm 68 by sub-assembly 16 as is well known in the art, which in the preferred embodiment includes a positive displacement pump. The dose of medication can be varied depending upon the substance used, which may, for example, include a cream which can take the pain out of getting vaccinations and other needle sticks such as EMLA™ (Eutectic Moisture of Local Anesthetics) Cream in the form of a combination of lidocaine and prilocaine in an oil and water emulsion and commercially available from Astra, Stockholm, Sweden. However, it should be appreciated that other substances suitable for being applied to the area may be utilized which are well known to those skilled in the art, including but not limited to TRH, Oxybutynin, Phenazocine, Scopolamine, Nivadipine, LHRH, Antimony bis(catechol-3,5-disulphonate), Niridazole, Metrifonat, Lidocaine hydrochloride, Hydrocortisone, Acetic acid, Penicillin, Dexamethasone sodium phosphate, Pilocarpine nitrate, Nitroglycerin, Progesterone, Estradiol, Ethynyl estradiol, Levonorgestrel, Isosbide dinitrate, Biperiden and the like.

Thereafter, the backing material and the tri-laminate material are brought together and heat sealed around the outer periphery of the dimple by sub-assembly 18 to form the continuous web 56, with each dose of medication being sealed within a corresponding dimple to form the reservoir 62. Next the continuous web is die cut to fabricate the patches 11 therefrom.

Figure 14:
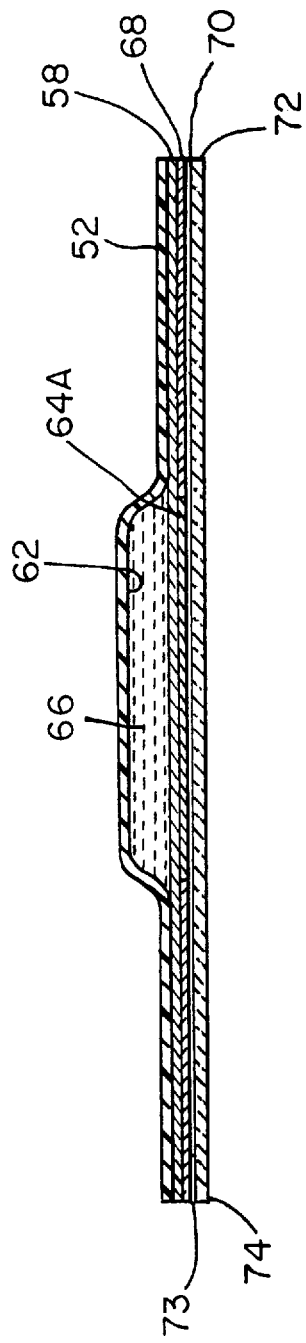
FIG. 14 is an enlarged, cross-sectional, side view of the patch of the present invention with the layer of non-woven material situated between the tri-laminate material and the dose of medication.
Figure 15:
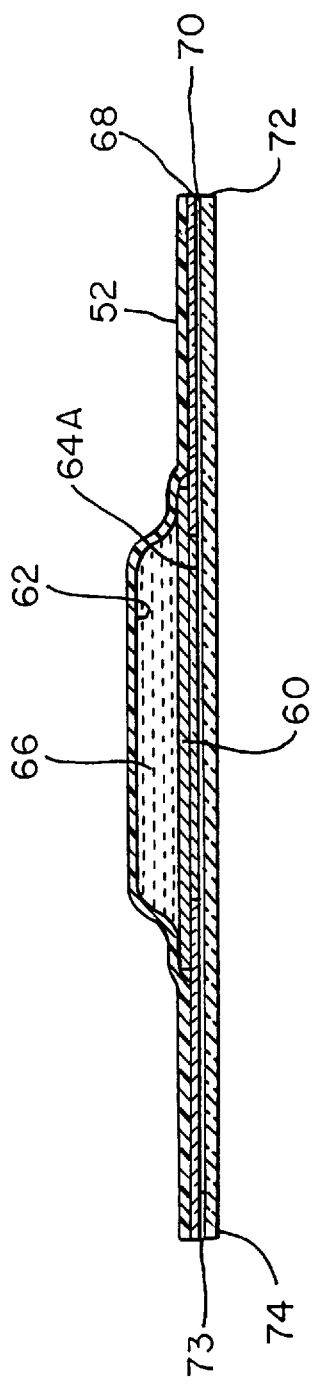
FIG. 15 is an enlarged, cross-sectional, side view of the patch of the present invention with the disc-shaped piece of porous material situated between the tri-laminate material and the dose of medication.

In the preferred embodiment of the apparatus 10A illustrated in FIG. 12 where similar components are identified by corresponding reference numerals, a layer of porous material 58 is feed by sub-assembly 21 between the layer of backing material 52 and the layer of tri-laminate material 54 prior to sub-assembly 16 placing the dose of medication on the web 56A. In addition, the sub-assembly 14 for forming the opening in the tri-laminate material is modified to include a single blade or circular cutter 48 having a kiss cut die shape as illustrated in FIG. 12A. In this way, at least one circular opening 64A is formed in the diaphragm 68 which corresponds to the opening of the cavity 28 of the reservoir 62 to permit passage of the medication from the reservoir 62 through the porous material 58 when the release liner 72 is peeled away from the patch 11A. The porous material is preferably a non-woven, heat-sealable polymeric material, such as for example, non-woven LDPE available from Poly-Bond, Inc., Waynesboro, Va. In this way, the layer of non-woven material 58 can be feed along one of the tracks of the apparatus 10A and applied as an integral part of the web 56A from which the patches 11A illustrated in FIG. 14 is cut, and the non-woven material 58 holds the medication back when the sheet of polyester film is peeled away from the patch.

Figure 13:
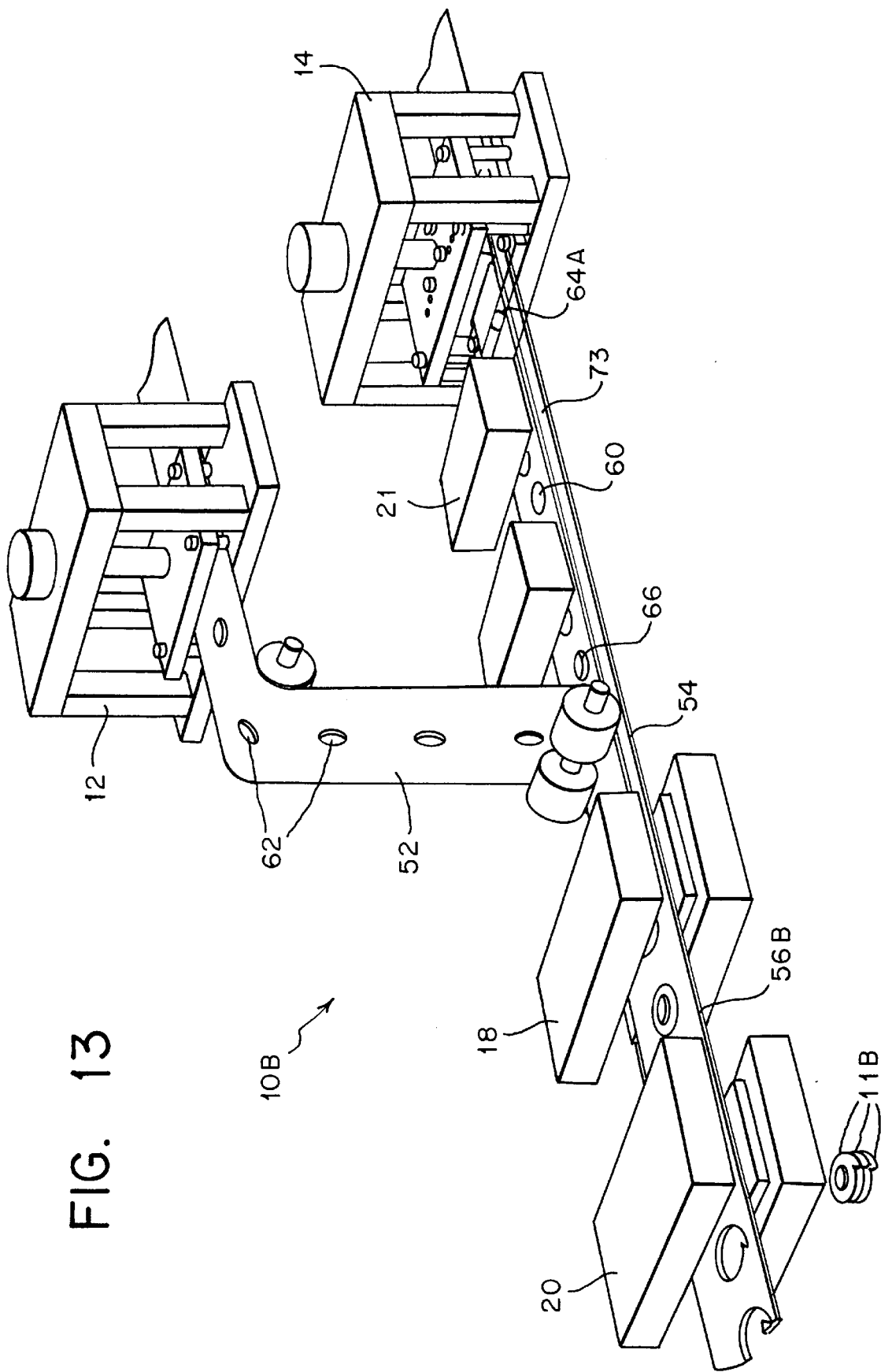
FIG. 13 is a perspective schematic view of an alternative embodiment of the apparatus of the system of the present invention illustrating the various steps for making the patches, including the step of placing a disc-shaped piece of a porous material on the tri-laminate material prior to placing the dose of medication thereon.

In the alternative embodiment of the apparatus 10B illustrated in FIG. 13, a disc-shaped piece of porous material 60 is placed by sub-assembly 21A on the layer of tri-laminate material 54 prior to sub-assembly 16 placing the dose of medication on the web 56B. In addition, the sub-assembly 14 for forming the opening in the tri-laminate material is also modified as in the case of the preferred embodiment previously discussed with respect to FIG. 12A so that at least one circular opening 64A is formed which corresponds to the opening of the cavity 28 of the reservoir 62, which can likewise be peeled away with the release liner. The disc-shaped piece of porous material 60 may include surgical gauze or a like material. In this way, the disc 60 holds the medication back when the sheet of polyester film is peeled away from the patch 11B illustrated in FIG. 15.

The material of which the diaphragm 68 is made in the various embodiments is spaced from the edge of the release liner to provide a free zone 73 without adhesive, with the spacers 40A, 40B and the cutting edge of each blade 38 or the cutter 48 being aligned such that when the top plate 34 and the bottom plate 32 are brought together with the tri-laminate material therebetween, extending portions 41A, 41B of the spacers come in contact with the release liner along the free zone 73 and do not come in contact with the material from which the diaphragm is made. In this way, advancement of the spacers, as well as the blade or cutter, is limited so that slitting or cutting of the tri-laminate material by the cutting edge is restricted to the diaphragm. In this way, slitting or cutting of the release liner 72 is prevented to provide a sealed medication. Also in this way, any irregularities resulting from variations in the thickness of the adhesive layer 70 and/or diaphragm 68 are compensated for or otherwise do not effect advancement of the cutting edge.

It should also be appreciated that other forms of cutting means may be utilized in connection with sub-assembly 14 to cut or otherwise form at least one opening in the diaphragm. For example, a cutter 48 as illustrated in FIG. 12A is preferred to form the circular opening by kiss-cutting the diaphragm material to form a circular slit surrounding a plug of diaphragm material. In this way, upon use of the patch, the plug of diaphragm covering the reservoir and porous material adhered to the adhesive is peeled away with the release liner to expose the opening. In the alternative, blades 38 having straight cutting edges may be used to form the openings as straight slits so that upon use of the patch, the diaphragm remains and covers the reservoir which might otherwise adhere to the adhesive and peel away with the release liner. In addition, the openings 64 may take other forms and shapes depending upon the application as well as the viscosity of the medication. For example, where the medication is a semi-rigid gel or hydrogel, the openings may merely be a single opening exposing either the complete reservoir or the porous material upon peeling the release liner from the patch.

The materials and components used for constructing the various sub-assemblies are not essential to the present invention and may be made from a variety of commercially available components well known to those skilled in the art. Normally, manufacturers of the present apparatus and patch will select the various materials and components, based upon price, availability and application. For example, the upper sheet of material of the tri-laminate may include any polymeric material or a membrane material.

Operation and Use

The operation of the system of the present invention in connection with the embodiment of the apparatus 10 illustrated in FIGS. 1 and 2 will now be explained with reference to the flow diagram shown in FIG. 11 illustrating the various stations making up the sub-assemblies 12, 14, 16, 18 and 20.

As explained, the backing material 52 and the tri-laminate material 54 are processed through the apparatus 10 along separate tracks through the sub-assembly 12 for forming the reservoir and the sub-assembly 14 for forming the openings in the diaphragm 68, with the dose of medication being applied to the tri-laminate material above the openings or by kiss-cutting. Thereafter, the two materials 52, 54 are brought together with the backing material 52 also overlapping the diaphragm 68 about the free zone and heat sealed by the sub-assembly 18 to form the continuous web 56 from which the patches 11 are die cut, which in the preferred embodiment includes a tab 74 extending into the free zone 73 for gripping and peeling the patch apart. Preferably, as illustrated in FIG. 13, the layer of porous material 58 includes a non-woven material of a polymeric material which may be feed along the same track as the tri-laminate to situate the layer of non-woven material on the tri-laminate material 54 prior to placing the dose of medication on the web so that the non-woven material is situated between the medication and the tri-laminate as an integral layer of the web for heat sealing the backing material, tri-laminate material and non-woven material together and cutting the various patches 11A therefrom. In addition, the non-woven material 58 holds the medication in place while the release liner is peeled from the patch for application of the medication to the applied area of the patient. In the way, the medication can then be forced through the non-woven material and applied to the patient.

Use of the patch of the present invention as illustrated in FIGS. 6–10 will now be explained. Initially, the patch is gripped by the tab 74 and pulled to remove the release liner 72 and to expose the medication for topical application. In one embodiment, a plurality of openings 64 in the form of slits are formed in the diaphragm parallel to the direction of peeling the release liner from the patch. In this way, the medication may be at least partially forced through the slits when the release liner is peeled from the patch to provide more intimate contact with the area to which the patch is to be applied and without tearing or ripping of the diaphragm as a result of the adhesive. In addition, upon peeling the release liner 72, the adhesive may be selected so that at least a portion remains on the diaphragm to increase adherence to the area, such as the skin of a patient, surrounding the area to which the medication is to be applied.

In addition, the patch of the present invention can be fabricated or otherwise cut from the continuous web in a number of shapes other than that shown in the drawings. Also, the patch can be made in different sizes depending upon whether it is to be used by adults or infants.

While the preferred embodiments of the present invention has been described so as to enable one skilled in the art to practice the systems, including the patches, apparatus and methods, of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A patch for applying a substance topically to an applied area, comprising:
    a trilaminate material including:
    a first material having a reservoir formed therein;
    wherein said reservoir is defined by dimple formed in said first material with a cavity therein;
    a dosage of medication contained in said reservoir; and
    a second material including a diaphragm covering said reservoir with a plurality of slits in said diaphragm through which the medication may pass for application to the applied area.

2. The patch defined in claim 1, further comprising a porous material situated between the second material and said dose of medication.

3. The patch defined in claim 2, wherein said porous material includes a layer of non-woven material.

4. The patch defined in claim 3, wherein said second material further includes a layer of an adhesive material and a release liner covering said layer of adhesive material with said adhesive material sandwiched between said release liner and said diaphragm.

5. The patch defined in claim 1, wherein at least either said first material or said second material includes a heat seal coating.

6. The patch defined in claim 1, wherein said reservoir is defined by a dimple formed in said first material with a cavity therein.

7. A method of making a patch for topically applying a substance to an applied area of a patient comprising the steps of:
    forming a reservoir in a backing material;
    cutting a plurality of slits in a diaphragm portion of a tri-laminate material said diaphragm layer covering said reservoir;
    placing a dose of medication on said tri-laminate material proximate said slits in said diaphragm;
    sealing said backing material and said tri-laminate material together to form a continuous web; and
    cutting a patch from said web.

8. The method of forming a patch defined in claim 7, further comprising the step of placing a porous material between said tri-laminate material and said backing material prior to placing said dose of medication on said tri-laminate material so that said porous material is situated between said dose of medication and said tri-laminate material.

9. The method of forming a patch defined in claim 8, wherein said step of placing said porous material includes feeding a layer of non-woven material.

10. The method of forming a patch defined in claim 7, wherein said step of sealing said backing material to said tri-laminate material incudes the step of forming a heat seal around a periphery of said reservoir.

11. The method of forming a patch defined in claim 7, wherein said step of cutting said patches from said continuous web includes die cutting.

12. The method of forming a patch defined in claim 7, further comprising the step of forming said reservoir in said backing material by applying a positive pressure to one side of said backing material.

13. A patch for applying a substance topically to an applied area, comprising:
    a trilaminate material including a first material having a reservoir formed therein,
    wherein said reservoir is defined by dimple formed in said first material with a cavity therein;
    a dosage of medication contained in said reservoir; and
    a second material including a diaphragm covering said reservoir with at least one slit formed in said diaphragm through which the medication may pass for application to the applied area,
    wherein said second material further includes a layer of adhesive material and a release liner covering said layer of adhesive material, with said adhesive material sandwiched between said release liner and said diaphragm.

14. The patch defined in claim 13, further comprising a porous material situated between the second material and said dose of medication.

15. The patch defined in claim 14, wherein said porous material includes a layer of non-woven material.

16. The patch defined in claim 13, wherein said at least one opening includes a plurality of slits formed in the diaphragm.

17. The patch defined in claim 13, wherein at least either said first material or said second material includes a heat seal coating.

18. The patch as recited in claim 1, wherein said medication in said reservoir is a transdermal medication.

19. A method in accordance with claim 7, wherein said medication is a transdermal medication.

20. A patch as recited in claim 13, wherein said medication in said reservoir is a transdermal medication.

\* \* \* \* \*